US006973449B2

(12) United States Patent
Meltzer

(10) Patent No.: US 6,973,449 B2
(45) Date of Patent: Dec. 6, 2005

(54) SYSTEM, METHOD OF PORTABLE USB KEY INTERFACED TO COMPUTER SYSTEM FOR FACILITATING THE RECOVERY AND/OR IDENTIFICATION OF A MISSING PERSON HAVING PERSON'S UNIQUE IDENTIFICATION, BIOLOGICAL INFORMATION

(75) Inventor: Andrew Mitchell Meltzer, Mt. Laurel, NJ (US)

(73) Assignee: National Association for Child Abduction Prevention, Medford, NJ (US)

(*) Notice: Subject to any disclaimer, the term of this patent is extended or adjusted under 35 U.S.C. 154(b) by 0 days.

(21) Appl. No.: 10/854,896

(22) Filed: May 27, 2004

(65) Prior Publication Data

US 2004/0243542 A1 Dec. 2, 2004

Related U.S. Application Data

(60) Provisional application No. 60/473,217, filed on May 27, 2003.

(51) Int. Cl.[7] .............................................. G06F 17/30
(52) U.S. Cl. .............................. 707/1; 707/10; 707/200; 340/573.3; 382/115
(58) Field of Search ..................... 707/1–3, 100–104.1, 707/200, 10; 709/203–228; 340/5.81, 7.48, 340/7.5, 7.53, 7.55, 7.59, 7.61–7.62, 10.6, 340/539.13, 573.1, 573.3, 573.4; 379/38.41; 705/3; 713/200–202; 348/158; 382/115, 382/181; 455/404.2

(56) References Cited

U.S. PATENT DOCUMENTS 5,568,406 A * 10/1996 Gerber ....................... 702/159

| 5,754,136 A | * | 5/1998 | Kojima et al. ......... 342/357.07 |
| 5,926,103 A | * | 7/1999 | Petite ..................... 340/825.19 |
| 5,955,952 A | * | 9/1999 | Bergman et al. ......... 340/573.1 |
| 5,983,238 A | * | 11/1999 | Becker et al. ........... 707/104.1 |
| 6,034,605 A | * | 3/2000 | March ..................... 340/573.1 |
| 6,044,349 A | * | 3/2000 | Tolopka et al. ................. 705/1 |

(Continued)

FOREIGN PATENT DOCUMENTS

WO     WO 99/41723    *   8/1999

(Continued)

OTHER PUBLICATIONS

Hinnrichs,M, "handheld imaging spectrometer", applied imagery pattern recognition workshop, proceedings, Oct. 31, 2002 pp 78-84.*

(Continued)

Primary Examiner—Srirama Channavajjala
(74) Attorney, Agent, or Firm—Cozen O'Connor; Michael B. Fein

(57) ABSTRACT

A system, method, and software for facilitating the identification and recovery of missing persons. In one aspect, the invention is a system comprising a portable device comprising a computer memory medium and means for interfacing with a computer system having a display device; a software program loaded on said computer memory medium, said software comprising means for receiving data indicative of a person's unique identification information, means for storing said received data on said computer memory medium, said computer memory containing data indicative of said person's unique identification information stored thereon, and means for displaying said stored data on said display device when said portable device is interfaced to the computer system. The invention stores all necessary data identification data for a person in a single location for ease of access and distribution to authorities in time of crisis.

23 Claims, 15 Drawing Sheets

U.S. PATENT DOCUMENTS

| | | | |
|---|---|---|---|
| 6,184,788 B1 * | 2/2001 | Middlemiss et al. | 340/568.7 |
| 6,241,668 B1 * | 6/2001 | Herzog | 600/407 |
| 6,449,611 B1 * | 9/2002 | Frankel et al. | 707/6 |
| 6,491,297 B1 * | 12/2002 | Cardoso | 273/138.1 |
| 6,671,358 B1 * | 12/2003 | Seidman et al. | 379/93.12 |
| 6,703,918 B1 * | 3/2004 | Kita | 340/5.52 |
| 2002/0039067 A1 * | 4/2002 | Eubanks | 340/573.1 |
| 2002/0064776 A1 * | 5/2002 | Liu et al. | 435/6 |
| 2002/0107947 A1 * | 8/2002 | Moragne et al. | 709/223 |
| 2002/0198473 A1 * | 12/2002 | Kumar et al. | 600/595 |
| 2003/0085274 A1 * | 5/2003 | Leaton et al. | 235/380 |
| 2003/0097351 A1 * | 5/2003 | Rothschild et al. | 707/1 |
| 2004/0093349 A1 * | 5/2004 | Buinevicius et al. | 707/104.1 |
| 2004/0104808 A1 * | 6/2004 | Khoshbin | 340/7.5 |
| 2004/0181676 A1 * | 9/2004 | Lane et al. | 713/182 |
| 2004/0186920 A1 * | 9/2004 | Birdwell et al. | 710/1 |
| 2004/0213437 A1 * | 10/2004 | Howard et al. | 382/115 |
| 2004/0243542 A1 * | 12/2004 | Meltzer | 707/1 |
| 2004/0260876 A1 * | 12/2004 | Singh et al. | 711/117 |
| 2005/0039014 A1 * | 2/2005 | Sajkowsky | 713/172 |
| 2005/0041863 A1 * | 2/2005 | Ray et al. | 382/181 |
| 2005/0091277 A1 * | 4/2005 | Desman | 707/104.1 |

FOREIGN PATENT DOCUMENTS

| | | | |
|---|---|---|---|
| WO | WO 01/24055 A1 * | 4/2001 | 17/30 |
| WO | WO 03/069365 A1 * | 8/2003 | 5/14 |

OTHER PUBLICATIONS

Koshima .H. et al. "personal locator services emerge", spectrum, IEEE, vol. 37, issue:2, pp 41-48.*

John Tonkyn, "california mising persons DNA program challenged with identifying thousands of human remains", applied biosystems, p. 1-2.*

Elizabeth Joyce, "pursuing the poer of DNA: forensic DNA's impact on crime victims and their advocates", national center for victims of crime, networks, winter/spring 2003, pp 1-7.*

University of north texas health science center at fort worth, Heath & science quarterly, 2003, winter: DNA technology renews search for missing persons 4 pages.*

Palafox,J.L problems of physiogonomic identification with video cameras, Security technology, proceedings, IEEE 1999, pp 21-25.*

Mi-Suen Lee, "detecting people in cluttered indoor scenes", computer vision and pattern recognition, 2000 proceedings, vol. 1, pp 804-809.*

Mathew Palakal et al. "an intelligent biological information management system", symposium on applied computing, proceedings of the 2002 ACM, session: Bioinformatics, pub:2002, pp 159-163.*

Stephen Cordner et al. "developing standards in international forensic work to identify missing peersons", RICR Dec. 2002, vol. 84, No. 848, pp 867-884.*

Saul Greenberg et al. "the notification collage: posting information to public and personal displays", conference on human factors in computing systems, proceedings of the SIGCHI, 2001, pp 514-521.*

Irma Van der ploeg "written on the body: Biometrics and identity", ACM SIGCAS computers and society, vol. 29, issue: 1, Mar. 1999, pp 37-44.*

* cited by examiner

SYSTEM, METHOD OF PORTABLE USB KEY INTERFACED TO COMPUTER SYSTEM FOR FACILITATING THE RECOVERY AND/OR IDENTIFICATION OF A MISSING PERSON HAVING PERSON'S UNIQUE IDENTIFICATION, BIOLOGICAL INFORMATION

CROSS-REFERENCE TO RELATED APPLICATION

This application claims the benefit of U.S. Provisional Patent Application 60/473,217, filed May 27, 2003, which is hereby incorporated by reference in its entirety.

FIELD OF THE INVENTION

The present invention relates generally to the field of systems and methods for facilitating the prevention, recovery and identification of missing persons, and specifically to software and computer-based systems and methods for facilitating such recovery and identification.

BACKGROUND OF THE INVENTION

In the case of abducted persons, according to the Federal Bureau of Investigation, the first two to three hours following a stranger abduction are the most critical to that person's survival. In this time it is imperative that accurate and up-to-date physical and biological data be provided to the proper authorities so that proper notice and comprehensive data can be promptly relayed to the community and/or other division of authority. However, the necessary physical and biological data of such persons is not easily and quickly accessible because the data is often stored in various locations and/or not stored anywhere at all. This problem is further complicated by the fact that during such situations, persons concerned about the abducted and/or missing person are/understandablyistraught, emotionally, and/or unable to think clearly enough to gather such information Moreover, a person can be abducted or become missing when the concerned persons are not at home or at a location where they do not have access to their personal belongings, including the necessary physical and biological data of the missing person. Lastly, as most abductions are carried out by a non custodial parent or known family members, every parent is a suspect when a child becomes missing or is believed to be abducted. Consequently, precious time is lost to police deposition before a proper search can be conducted. Having all of a missing person's information in a consolidated and accessible form can aid authorities in conducting an immediate search while the parent is questioned and hopefully cleared of any wrong doing.

Such problems exist not only in the case of abducted children, but can also delay identification and recovery efforts in situations arising from natural or man made catastrophe, terrorist act, or otherwise act of war.

DISCLOSURE OF THE INVENTION

It is therefore an object of the present invention to provide a system, method, and software for facilitating the identification and or recovery of a missing person.

Another object of the present invention to provide a system, method, and software for facilitating the identification or recovery of a missing person that stores the missing person's physical and biological information in a single location.

Yet another object of the present invention to provide a system, method, and software for facilitating the identification or recovery of a missing person that reduces the amount of time needed to furnish the missing person's physical and biological information to the necessary authorities.

Still another object of the present invention to provide a system, method, and software for facilitating the identification or recovery of a missing person that stores the missing person's physical and biological information in a portable medium.

A further object of the present invention to provide a system, method, and software for facilitating the identification or recovery of a missing person that reduces the amount of time needed to compile the missing person's physical and biological information.

A still further object of the present invention to provide a system, method, and software for facilitating the identification or recovery of a missing person that allows for time-efficient distribution of the missing person's physical and biological information by electronic distribution, e.g., via the Amber Alert Broadcast Network, the Internet, or by installing a portable device storing the missing person's information into an internal or external computer hard drive and accessing the stored information.

These and other objects are met by the present invention which in one aspect is a system for facilitating the identification or recovery of a missing person comprising: a portable device comprising a computer memory medium and means for interfacing with a computer system having a display device; a software program loaded on the computer memory medium, the software comprising means for receiving data indicative of a person's unique identification information, means for storing the received data on the computer memory medium, the computer memory containing data indicative of the person's unique identification information stored thereon, and means for displaying the stored data on the display device when the portable device is interfaced to the computer system. The unique identification information can comprise the missing person's personal and biological information, such as fingerprints, photographs, video, audio, DNA information, medical history, name, age, height, weight, eye color, and color of hair. The system accelerates recovery and/or identification of the missing person by compiling and storing all of the missing person's unique identification information into one single location, the computer memory of the portable device.

The portable device can be a writable DVD, diskette, CD, or a USB portable device, such as a USB key or a USB pen. Preferably, the portable device can be incorporated into and further comprise a key chain. The present invention will increase survival rates of stranger abducted children by reducing the amount of time needed to compile and ultimately furnish information to the Police and/or recovery/investigative teams. The software-based identification system can also be used to unite and inform surviving family members suddenly displaced from their home and or separated from each other due to a natural or man made catastrophe, terrorist act, or otherwise act of war.

The system of the present invention provides instant access to the missing person's unique identification information and serves to protect and recover missing family members negatively impacted, displaced and or separated. Preferably, the system will be distributed in conjunction with the Homeland Security Act.

The portable device can be operably connected to any internal or external computer hard drive and the software program can be executed, thereby accessing the computer memory of the portable device and retrieving the stored unique identification information and displaying the information on a display module connected to the computer hard drive. In the event a person whose unique identification information is stored on the system becomes missing, the portable device is preferably coupled to a computer hard drive that is connect to a network, such as the Internet, allowing for uploading of the missing person's unique identification information to the necessary authorities and/or agencies, thereby affording instant or near instant distribution of the information by electronic distribution. Such electronic distribution can be facilitated by email or other instantaneous electronic means.

The stored unique identification information can be inputted or updated by operably coupling the portable device to the computer hard drive in a similar manner and inputting data via a keyboard or other user input device such as a mouse. The computer memory of the portable device can be secured by password protection or other encryption means.

Additionally, the unique identification information of the missing person can be uploaded to a digital database for storage. In such an embodiment, it is preferred that the information be uploaded in a secure encrypted environment that is encrypted at the gateway and at the data storage point. In one embodiment, the software is stored on a server connected to the Internet and downloadable to the computer memory of the portable device when the portable device is operably coupled to a networked computer hard drive.

The software contains all of the code necessary to carry out the following functions and display the associated interfaces on a computer display module. Preferably, the software comprises code for facilitating the display of a user interface that comprises a plurality of templates having data entry fields in which a user can input a desired person's unique identification information via keyboard. Data entry fields are preferably provided for receiving data indicative of a person's name, nickname, address, social security number, birth date, gender, nationality, native language, guardian's address, guardian's name, and guardian's phone number. Additionally, the means for storing the inputted data can be a save data button located within the user interface. When the save button is activated, the data that has been inputted into the data entry fields is stored on the computer memory medium of the portable device. Each of the templates can comprise a window for displaying information and/or instruction for completing the specific template being displayed.

In order to ensure that the unique identification of the person whose data is stored on the portable device is current, the user interface preferably comprises a section that displays an expiration date for the stored data. It is further preferable that one of the templates comprise a window for displaying safety tips, useful web-links and/or a message from a sponsor. Moreover, an additional template is preferably provided that has data entry fields for receiving data indicative of a person's eye color, hair color, length of hair, hair style, facial hair, height, weight, build size, skin color, complexion, birth marks, identifying scars, identifying marks, physical disabilities, and mental disabilities. This template can further comprises a window for displaying informational statistics relating to missing persons and an automated time and date stamp that is automatically updated when data is entered into the template and stored.

The system also preferably comprises a template having data entry fields for receiving digital photographs of the person, digital fingerprints of the person, digital video of the person, or digital audio clips of the person. This template can further comprise a window for displaying instructions for importing the digital photographs, the digital fingerprints, the digital video, and the digital audio clips into the data entry field of the template. It is further preferable that upon importation of the digital photograph into the data entry field of this template that the digital photograph be automatically sized to fit in the corresponding data entry field.

The interface also preferably comprises another template having a data entry fields for receiving data indicative of a person's DNA sequence. Another template can be provided that has links to websites providing safety and/or abduction prevention information. Still another template can be provided that has data entry fields for receiving data indicative of a person's medical history. Yet another template can be provided having data entry fields for receiving data indicative of telephone numbers to contacts in the event of an abduction. Any of the templates can be designed to have a window displaying a sponsor's message and/or information.

The interface also preferably has a template for receiving missing information data in the event the person goes missing. In this event, the software preferably comprises means to automatically create an electronic poster based on the unique identification information stored and the missing information data inputted. It is further preferable that upon creation, the electronic poster is saved on the computer memory medium of the portable device as a single file that can be printed or electronically transferred when the portable device is interfaced with a computer hard drive.

In another aspect, the invention is a method of facilitating the recovery of a missing person comprising: downloading a software program to a portable device comprising a computer memory medium and means for interfacing with a computer system having a display device, the software comprising means for receiving data indicative of a person's unique identification information, means for storing the received data on the computer memory medium, the computer memory containing data indicative of the person's unique identification information stored thereon, and means for displaying the stored data on the display device when the portable device is interfaced to the computer system; interfacing the portable device to a computer system having a display device; and displaying the person's unique identification information on the display device.

In another aspect, the invention contains an output feature for composing and printing out identification cards that can be carried in a pocket, wallet or purse. The identification card contains vital information about a person for identification and or proper medical treatment of the individual featured on the identification card. The identification card will also bear telephone contact information of a parent/guardian or nearest relative.

In another aspect, the invention contains another such output feature that allows for the generation and printing of a missing person's poster. Such poster can be outputted in the form of a display poster or can be sent electronically sent via fax, email or other electronic medium. Such poster shall contain the missing or abducted person's vital characteristics and any known suspect information and facts surrounding the person's disappearance.

BRIEF DESCRIPTION OF THE DRAWINGS

FIG. 3 illustrates the user interface displaying a vitals template according to an embodiment of the present invention.

FIG. 12 illustrates the user interface displaying a contacts template according to an embodiment of the present invention.

MODES FOR CARRYING OUT THE INVENTION

Figure 1:
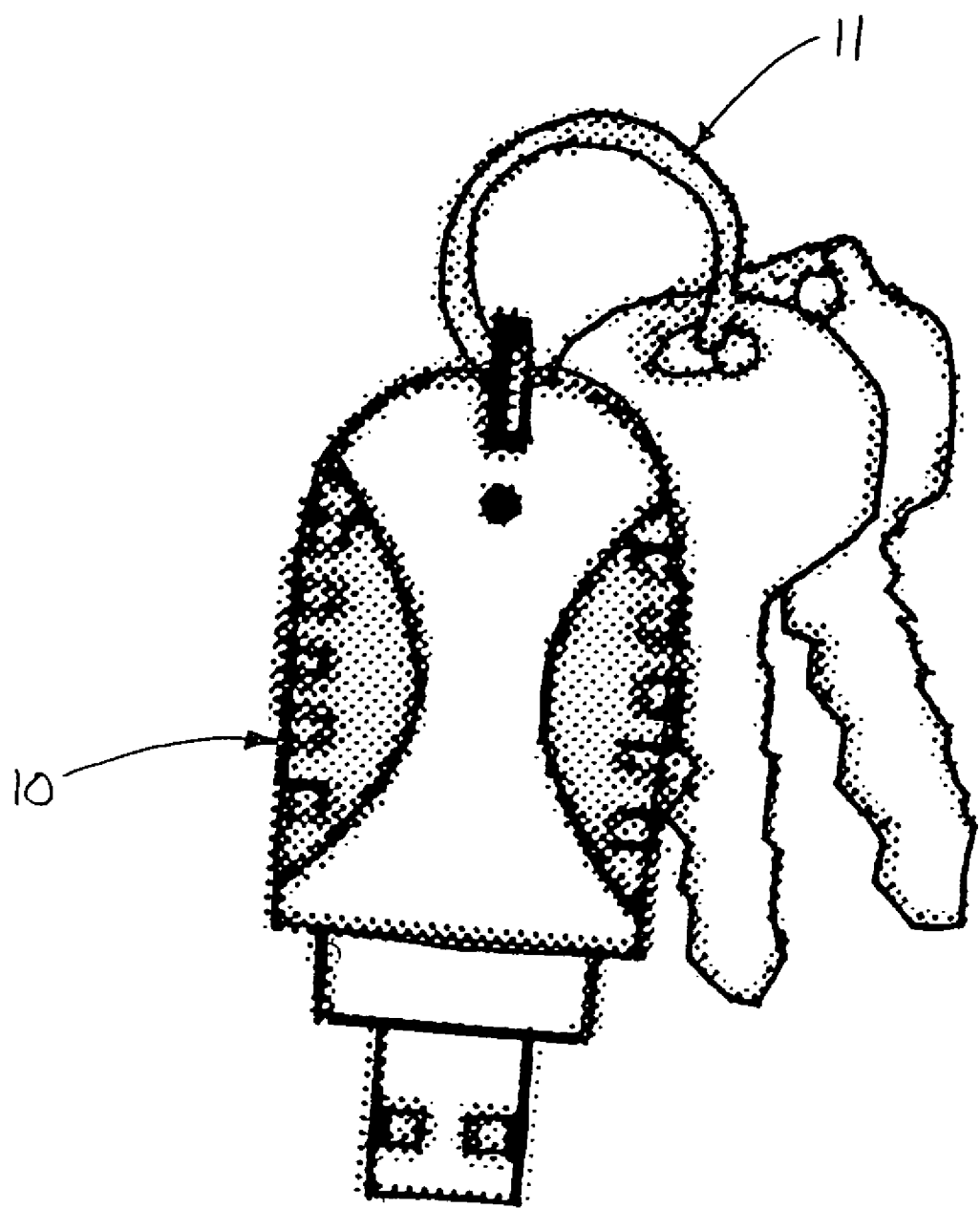
FIG. 1 is a perspective view of a portable USB key according to an embodiment of the present invention.
Figure 15:
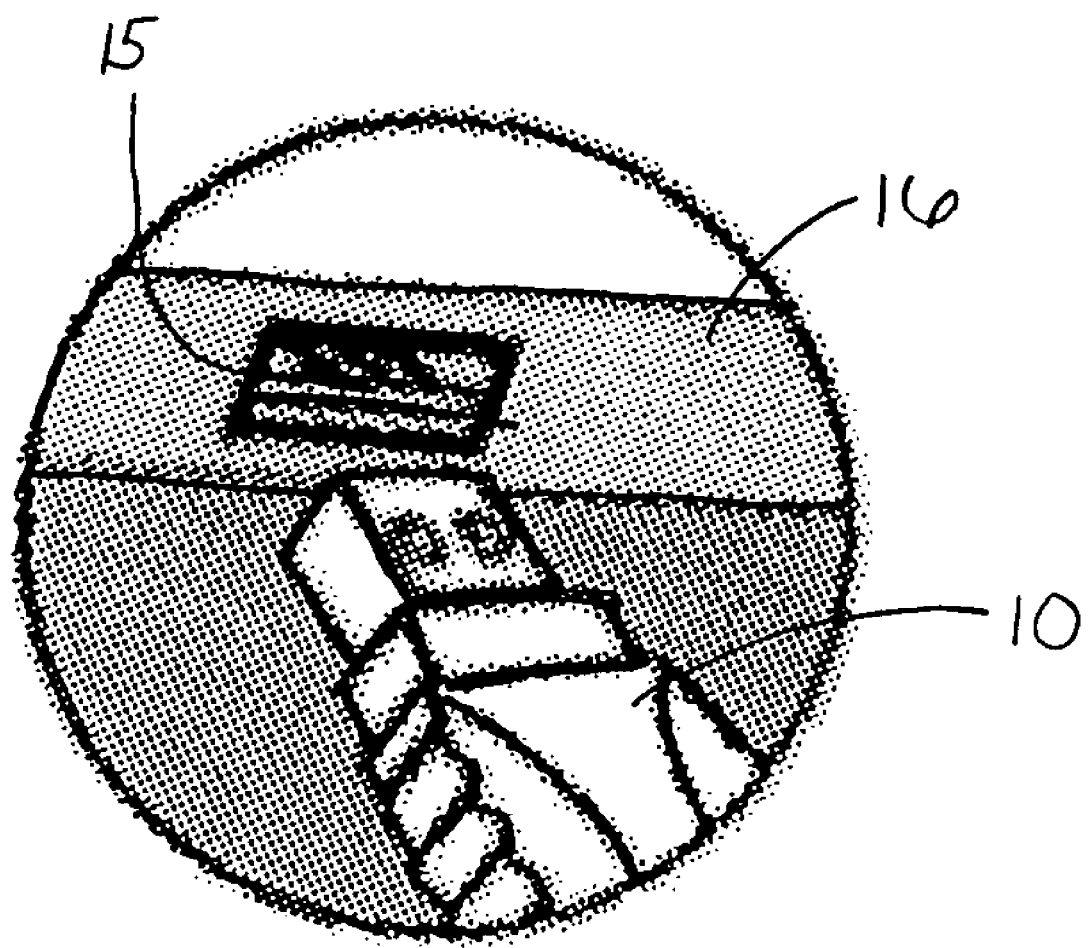
FIG. 15 is a perspective view of the USB key of FIG. 1 being inserted into the USB port of a computer hard drive.

FIG. 1 illustrates portable USB key 10 according to an embodiment of the invention. Portable USB key 10 comprises an internal computer memory medium (not illustrated) for data storage and retrieval. Portable USB key 10 is connected to key chain 11. Portable USB key 10 is a standard USB key that can be operably coupled to USB port 15 of computer hard drive 16 (FIG. 15). When coupled to USB port 15 of computer hard drive 16, computer hard drive 16 can access and retrieve data stored on the USB key's 10 internal computer memory medium. The stored data can then be displayed on a display module, such a computer monitor, that is coupled to the hard drive. Additionally, computer hard drive 16 can transmit and store/write data to the internal computer memory medium of portable USB key 10 when portable USB key 10 is interfaced with hard drive 16.

Stored on the computer memory medium of portable USB key 10 is software containing the computer code necessary to execute and display the interface and templates illustrated in FIGS. 2–14. The software also includes the computer code necessary to perform all of the associated functions. The software can be distributed for loading onto the computer memory medium of USB key 10 in several ways, including but not limited to downloading from affiliated websites, point of purchase at affiliated retailers, electronic kiosk locations, or independent distribution through marketing organizations. The software is preferably customizable. The USB key 10 can also have the software preloaded thereon and distributed at retailer outlets. The software is compatible with any Windows, MAC, or Linux operating systems and can be updated, printed, imported, exported, or stored electronically. Access to the software and/or computer memory medium is pass-coded to avoid unauthorized access and use. It can be further encrypted for additional protection. The identification scheme incorporated by the software is compatible with the Amber Alert Network and the Homeland Security Initiative security protocol. A user can also elect to transfer, copy, and/or store text files associated with the software on a separate floppy.

The software is compatible with encrypted web based service bureaus that will allow for the uploading, encrypted/secure storing, and retrieving of personalized digital and text information/data. Such uploading, storing, and/or retrieving can be accomplished electronically via a secure Internet connection and pass-coded entry. Uploaded and stored information may be utilized to aid medical emergency crews, law enforcement and FBI in locating a missing child, or treating an emergency victim with information contained in the software. Electronic retrieval of stored personal information from any affiliated web based service bureau using secure 128 bit encryption or higher as a standard security protocol is allowed.

When the software is loaded onto the computer memory medium of USB key 10 and accessed by computer hard drive 16, the interface and templates of FIGS. 2–14 are displayed on the computer's monitor. The various templates illustrated in FIGS. 2–14 are accessed by depressing an graphic tab in the interface. These interface and templates, and their functions, will now be discussed in turn.

Figure 2:
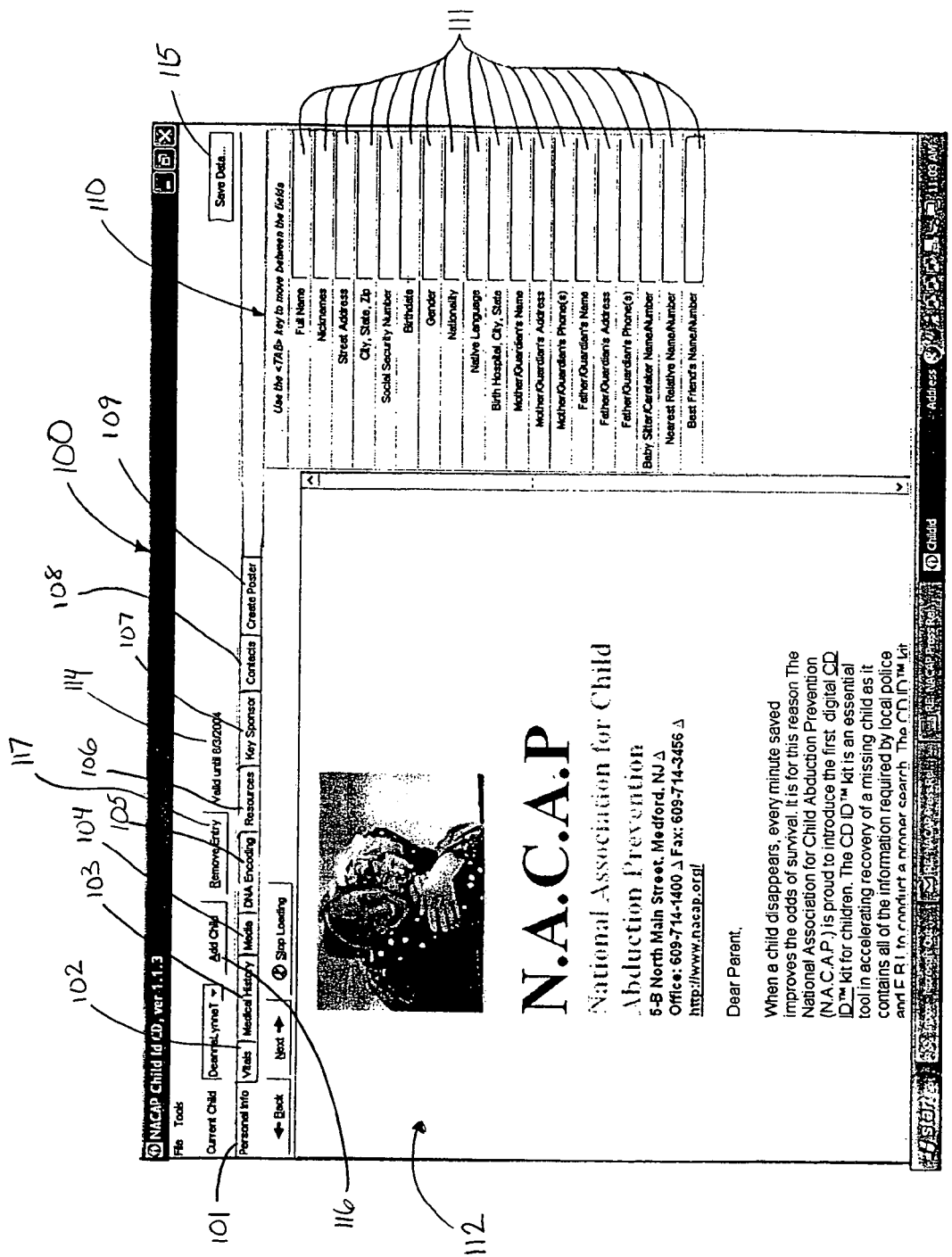
FIG. 2 illustrates a user interface displaying a personal information template according to an embodiment of the present invention.

Referring to FIG. 2, graphic user interface 100 is illustrated. Graphic user interface 100 comprises a number of tabs 101–109 that, when activated by a user, displays an associated template in the interface 100. In FIG. 2, personal information tab 101 is activated, thereby displaying personal information template 110 in interface 100. Personal information template 110 comprises a plurality of data entry fields 111 for receiving data inputted by a user that relates to a child's or family member's basic and personal information, such as name, nickname, address, social security number, birth date, gender, nationality, native language, guardian's address, guardian's name, and guardian's phone number. This data is designed to comprehensively capture the child's basic information and the parent's or legal guardian's contact information. A user inputs the data into data entry fields 111 via a keyboard, mouse, or other input device. The end user populates data entry fields 111 by depressing the tab key on a keyboard each time a field 111 is completed. The inputted data can be updated at any time. Template 110 also allows for a mother, father and or guardian's separate and specific information. Template 110 further comprises a window 112 for posting a sponsor's message or important safety tips.

When the user completes inputting data into all of the data entry fields 111, he/she activates save data button 115 located in the header of interface 100. When save data button 115 is activated, the data that was inputted into data entry fields 111 by the user is transmitted and stored on the computer memory medium of USB key 10. Data is saved in a format so that it can be displayed in the corresponding data entry fields upon retrieval.

The header of interface 100 also displays an expiration date and a version create date 114 that is inputted by the user.

The user can add additional children or family members at anytime, simply by depressing the add child button 116 located in the header of interface 100. Similarly, the user can eliminate a person's entry by depressing the remove entry button 117. Add child button 116 and remove entry button 117 remain accessible regardless of what template is displayed. Lastly, once the user has populated information in a template, it is possible to backup saved information to any internal or external drive by depressing the create disk button.

Figure 03:
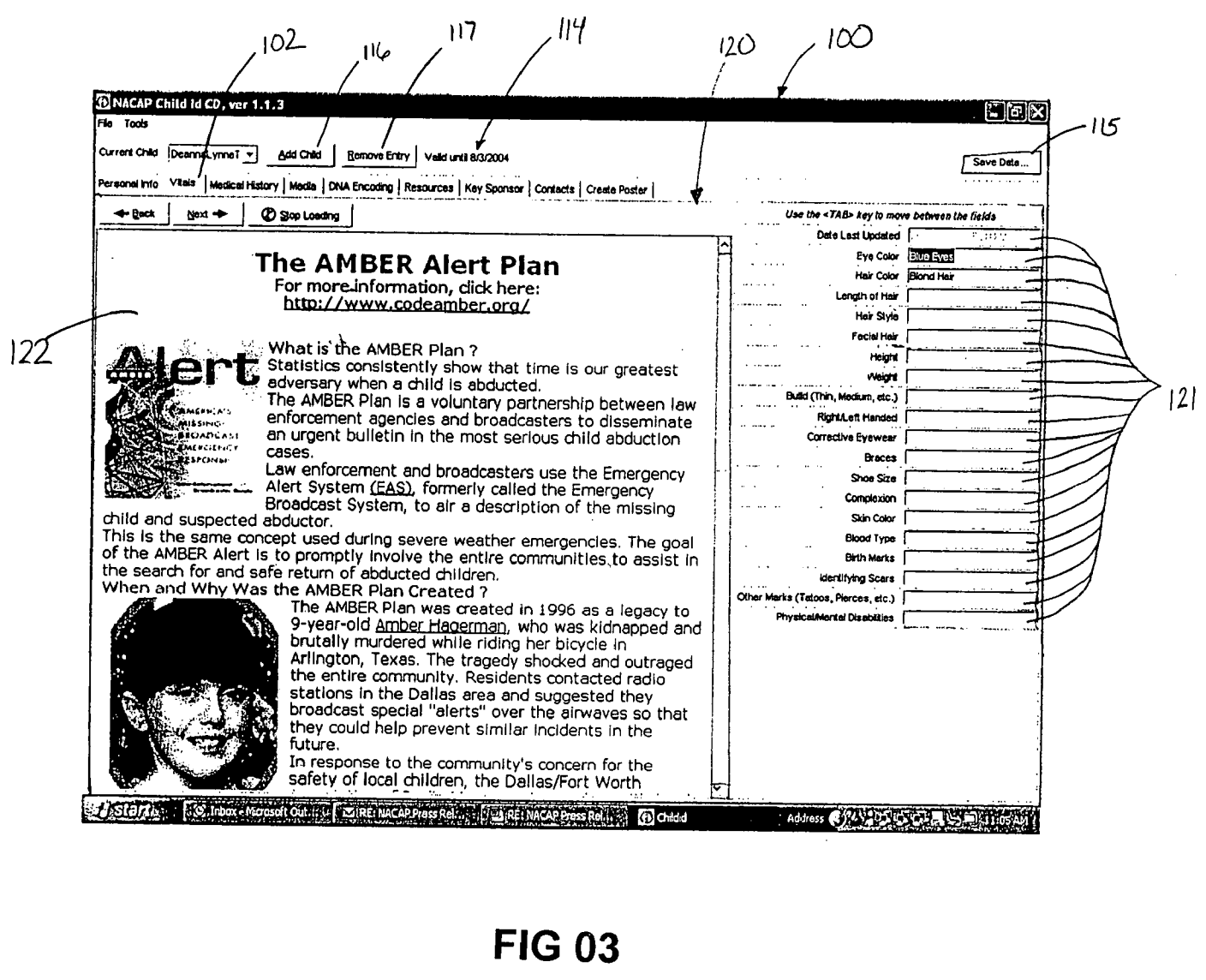

Referring now to FIG. 3, graphic user interface 100 is illustrated with vitals tab 102 activated, thereby displaying vitals template 120 in interface 100. Vitals template 110 comprises a plurality of data entry fields 121 for receiving data inputted by a user that relates to a child's pertinent and vital information, such as, height, weight, shoe size, eye color, blood type, identifying scars, physical/mental handicaps, or any characteristic that generally stays static. All of the fields are useful in properly identifying a emergency victim or missing child/other family member. There is an automatic time and date stamp feature that populates in the first data entry field 121 of the template 120, once the user inputs and saves that data. This is used to track the aging of the information recorded. Left window 122 of template 120 can be customized. As illustrated, an html file/web page is imbedded for informational purposes.

When the user completes inputting data into all of the data entry fields 121, he/she activates save data button 115 located in the header of interface 100. When save data button 115 is activated, the data that was inputted into data entry fields 121 by the user is transmitted and stored on the computer memory medium of USB key 10. Data is saved in a format so that it can be displayed in the corresponding data entry fields 121 upon retrieval.

Referring now to FIGS. 4–7, user interface 100 is illustrated with media tab 104 activated. When media tab 104 is activated, templates 130, 140, 150, and 160 for importing and exporting digital photographs, digital fingerprints, digital video and audio clips can be accessed. The various templates 130, 140, 150, and 160 of the media tab 104 are accessible via a second set of tabs 135–138 located at the bottom of template 130.

Figure 4:
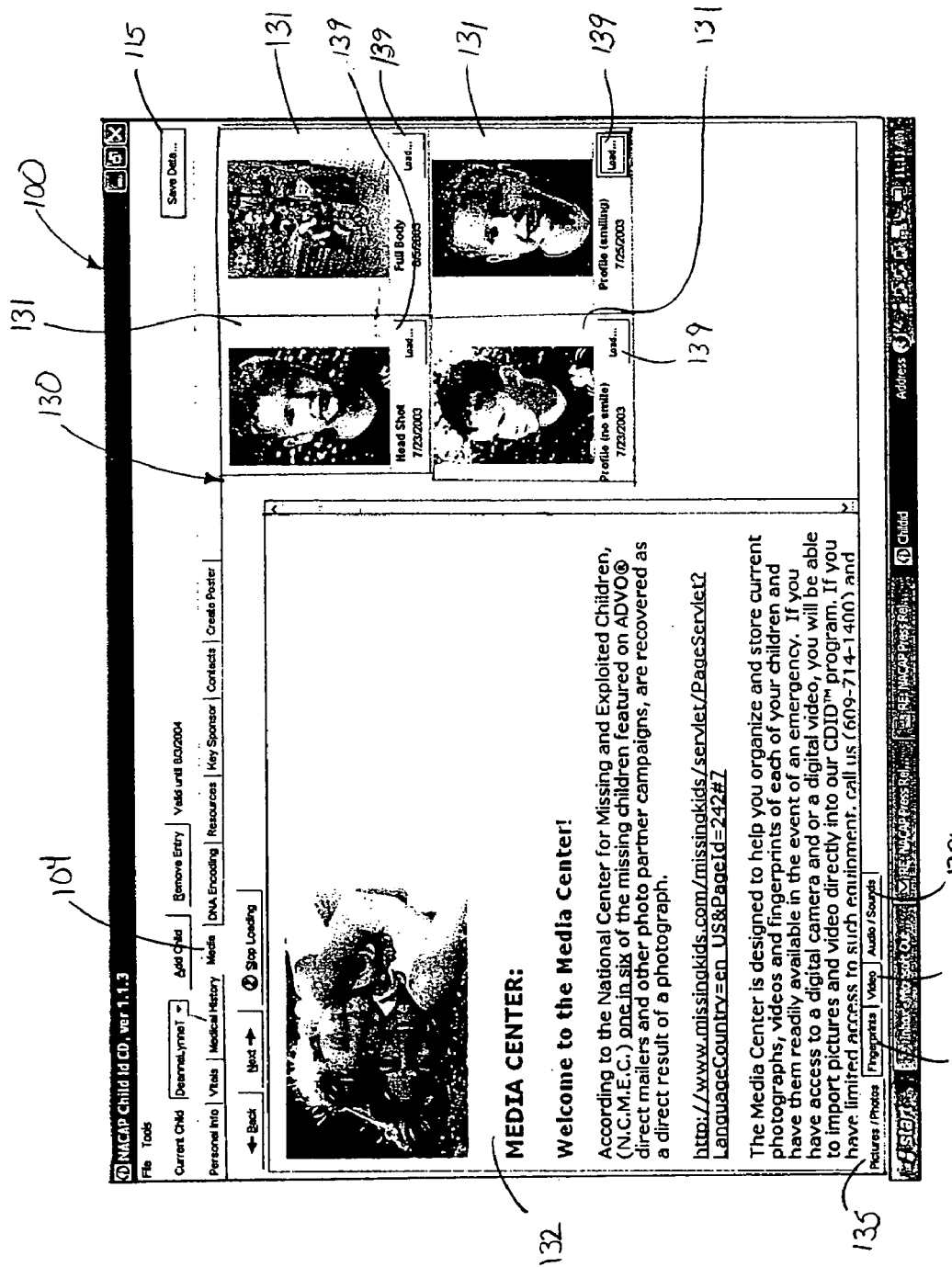
FIG. 4 illustrates the user interface displaying a digital photograph importation template according to an embodiment of the present invention.

FIG. 4 illustrates picture/photo tab 135 activated, thus displaying digital photograph importation template 130. Digital photographs can be imported into photo window templates 131 located to the right of the template 130. The software is designed to automatically size each photo to the window 131 once the photo file has been loaded. Photographs can be imported from any internal or external drive by activating the load button 139 to the right of the picture window 131. A variety of file types can be imported/loaded into the picture window 131, including but not limited to: Jpeg Image files (ipg), Jpeg Image files, (ipeg) Bitmaps (bmp), Icons (ico), enhanced metafiles (emf), and metafiles (wmf). The automatic picture sizing feature during picture loading eliminates the need for the end user to know how to manipulate or size the imported image. Each picture window 131 is characterized by picture type (Head Shot, Full Body, Profile (no smile), Profile (smiling) and contains an actual "create date" below the picture window 131, when the photograph was originally taken. Template 130 further comprises window 132 which can be used to display instructions for loading the photographs or other sponsored message or links.

When the user completes loading photographs into windows 131, he/she activates save data button 115 located in the header of interface 100. When save data button 115 is activated, the loaded photograph files are transmitted and stored on the computer memory medium of USB key 10. The photographs are saved in a format so that it can be displayed in the corresponding window 131 upon retrieval.

Figure 5:
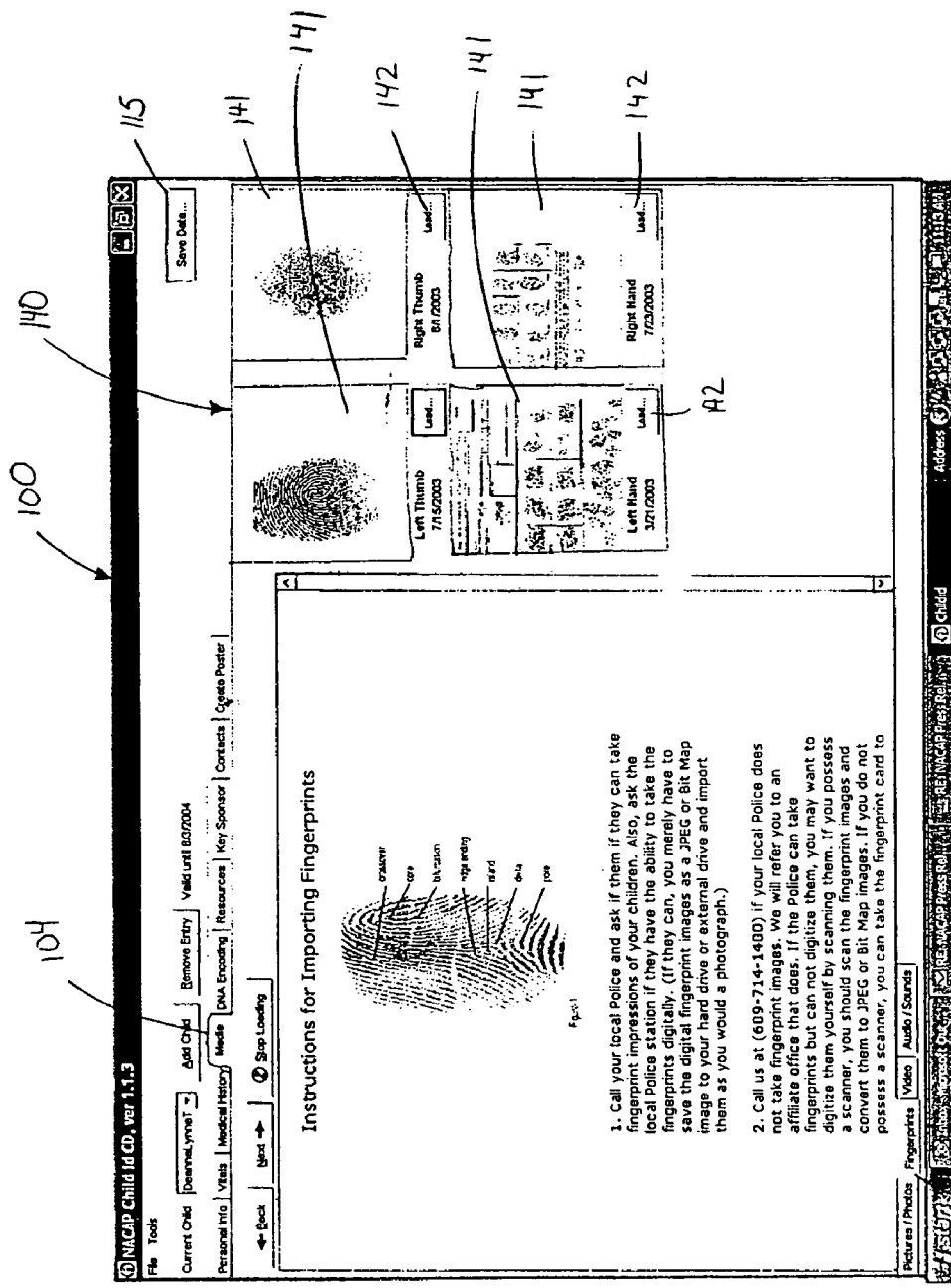
FIG. 5 illustrates the user interface displaying a fingerprint importation template according to an embodiment of the present invention.

FIG. 5 illustrates user interface 100 with media tab 104 activated and having fingerprint tab 136 also activated, thereby displaying fingerprint importation template 140. Fingerprint importation template 140 comprises a plurality of fingerprint windows 141 for receiving and exporting user inputted fingerprint information on a person. The top fingerprint windows 141 are for thumb prints only, while the bottom windows 141 feature the entire left and right hand. Any window 141 can be opened by depressing the load key 142 to the right of each window 141. A variety of file types can also be imported/loaded into the fingerprint window to include but not limited to: Jpeg Image files (ipg), Jpeg Image files, (ipeg) Bitmaps (bmp), Icons (ico), enhanced metafiles (emf), and metafiles (wmf) Note, all fingerprint images once imported are time and date stamped in accordance with the original create date of the image.

When the user completes loading photographs into windows 131, he/she activates save data button 115 located in the header of interface 100. When save data button 115 is activated, the loaded photograph files are transmitted and stored on the computer memory medium of USB key 10. The photographs are saved in a format so that they can be displayed in the correct windows 131 upon retrieval.

Figure 6:
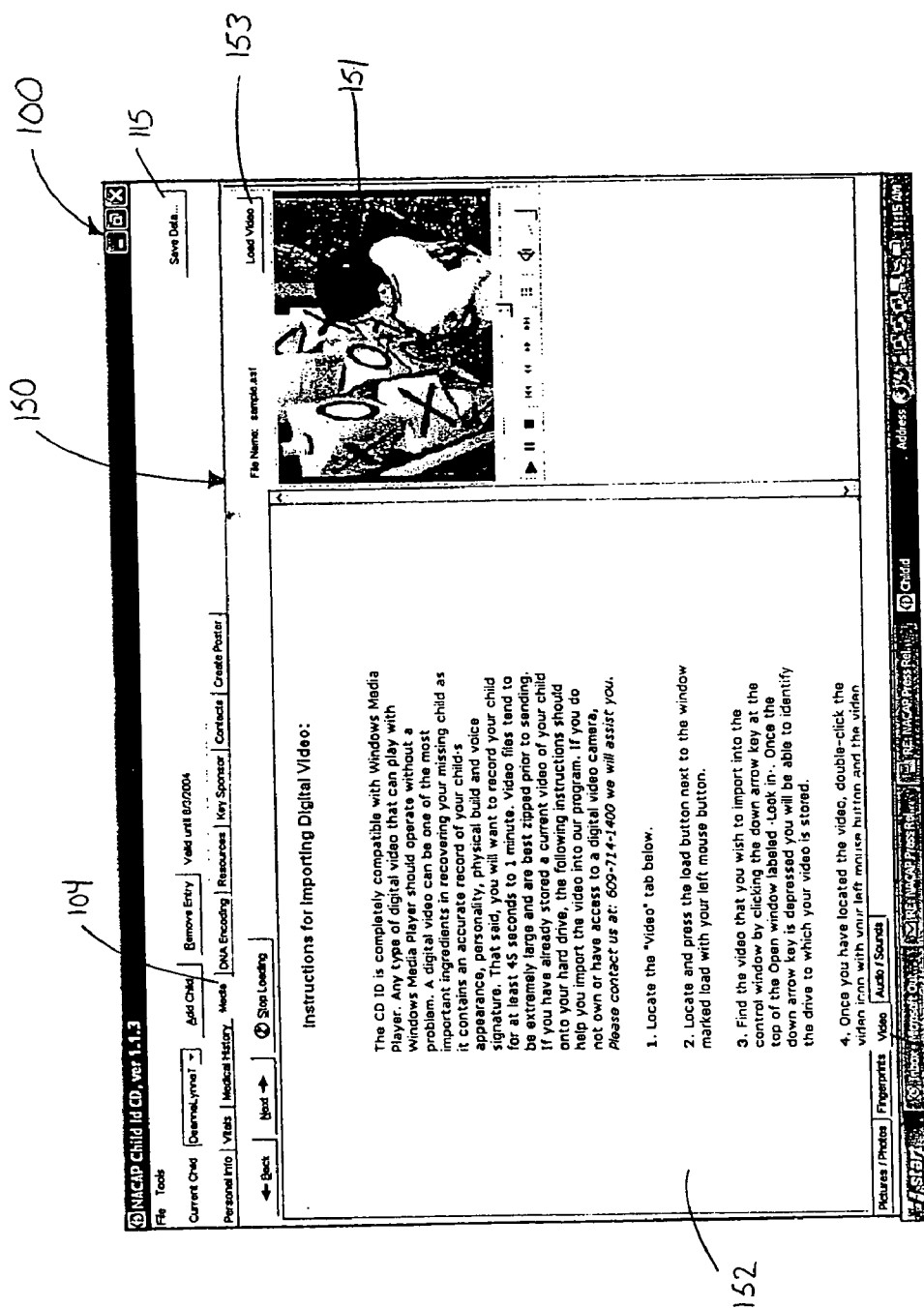
FIG. 6 illustrates the user interface displaying a digital video importation template according to an embodiment of the present invention.

FIG. 6 illustrates user interface 100 with media tab 104 activated and having video tab 137 also activated, thereby displaying digital video importation template 150. Video importation template template 150 comprises a windows 151 for importing/receiving and exporting a digital video. The load video button 153, when activated, allows for the user to import video of a variety of formats, including but not limited to: wav files, flash media and all formats compatible with Windows Media Player.

When the user completes loading video into window 151, he/she activates save data button 115 located in the header of interface 100. When save data button 115 is activated, the loaded video is transmitted and stored on the computer memory medium of USB key 10.

Figure 7:
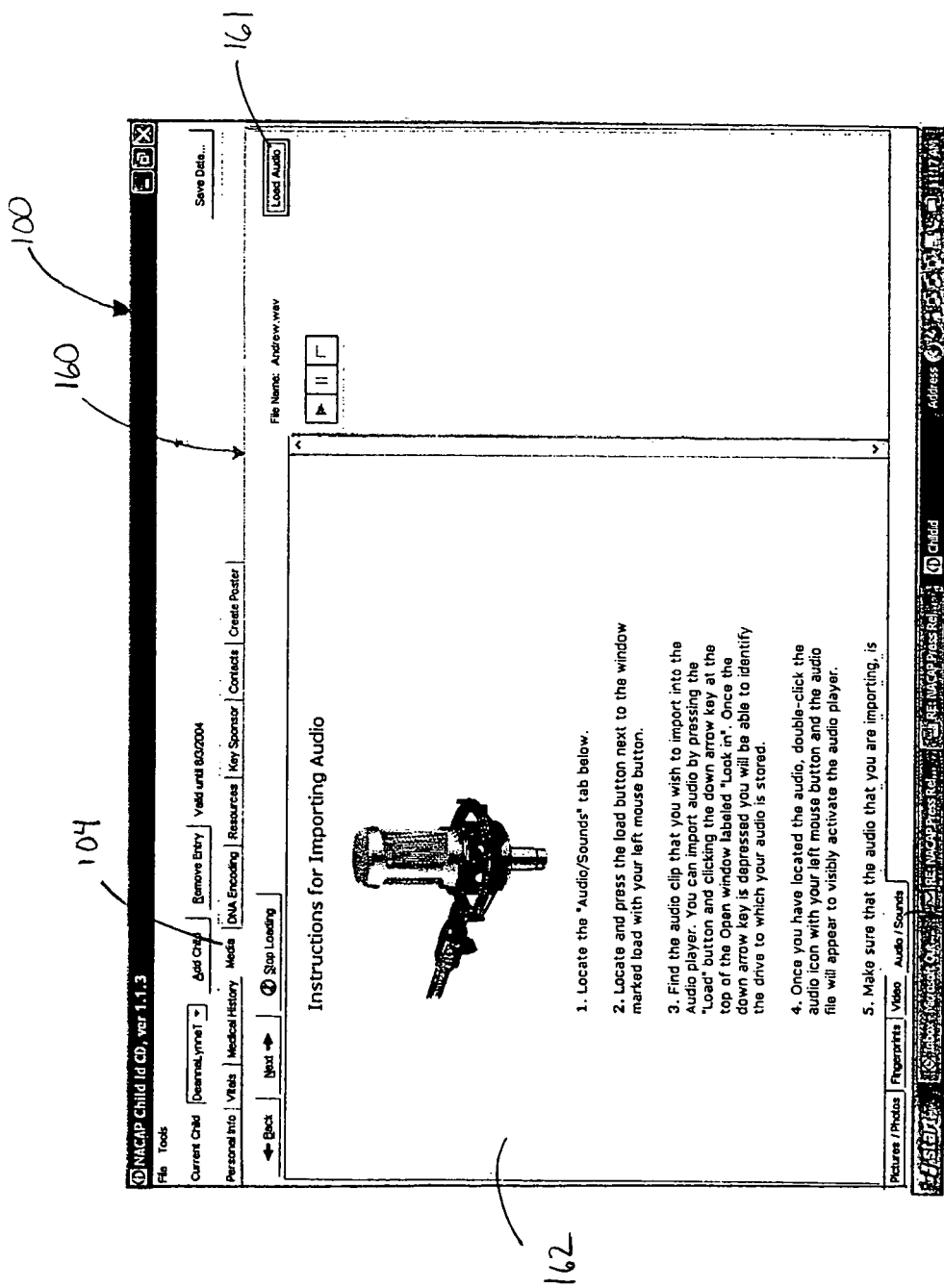
FIG. 7 illustrates the user interface displaying a audio importation template according to an embodiment of the present invention.

FIG. 7 illustrates user interface 100 with media tab 104 activated and having audio/sounds tab 138 also activated, thereby displaying audio importation template 160. The user can import audio files from any internal or external hard drive or create a new audio file by connecting a microphone to the computer in use. An audio file is received/imported by a user activating the load button 161. The file is saved to the computer memory medium of the USB key upon importation.

Figure 8:
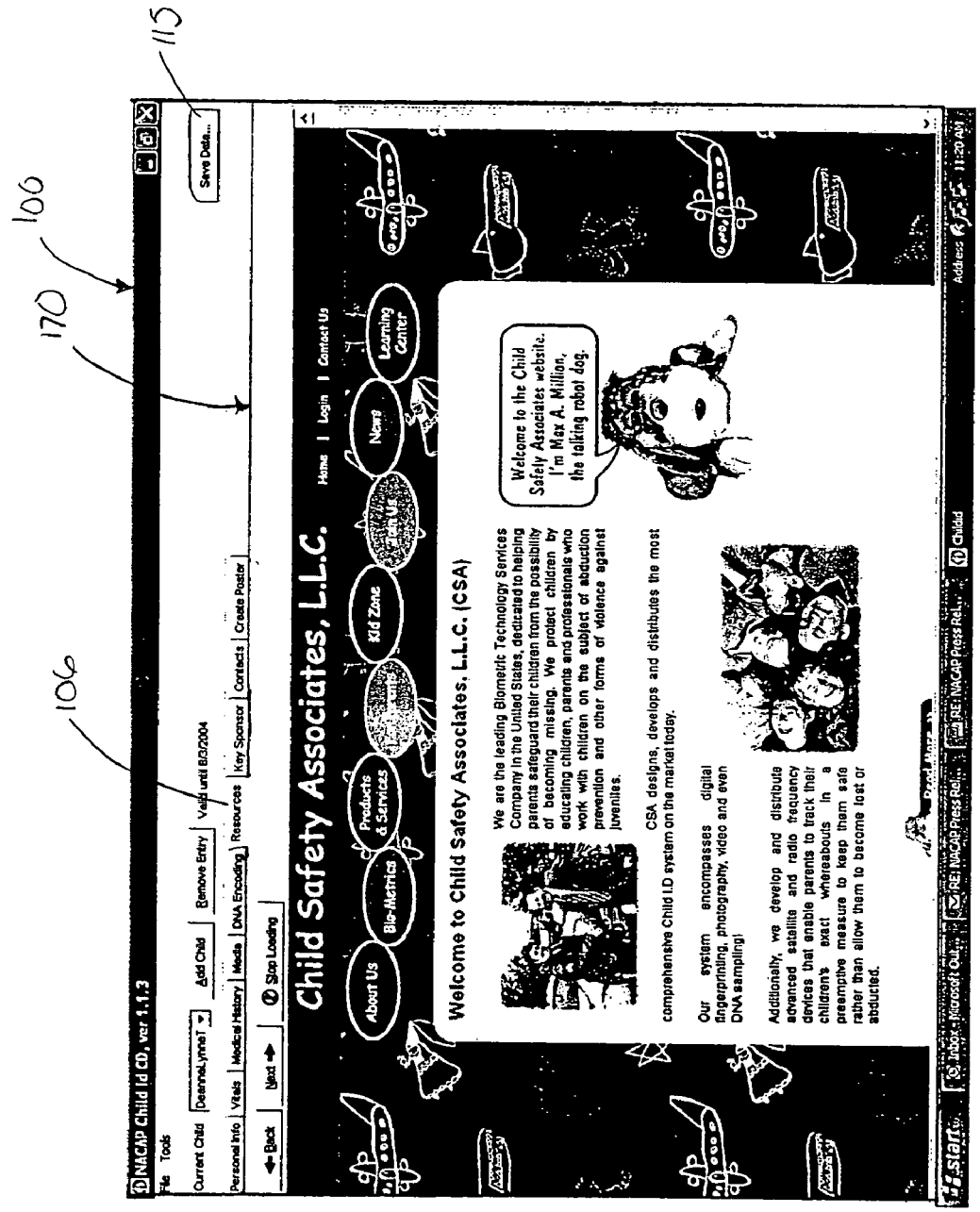
FIG. 8 illustrates the user interface displaying a resources template according to an embodiment of the present invention.

Referring now to FIG. 8, user interface 100 is illustrated with resources tab 106 activated, thereby displaying resources template 170 in interface 100. Resources template 170 displays safety web links that will provide useful safety and abduction prevention tips. If the computer in which USB key 110 is interfaced is connected to the Internet at the time of use, the window will open in a web browser so as to allow the end-user to navigate to different areas of interest on the web page. The Homeland Security version of this CD/DVD/PORTABLE STORAGE-MEMORY DEVICE will feature safety survival tips and web links.

Figure 9:
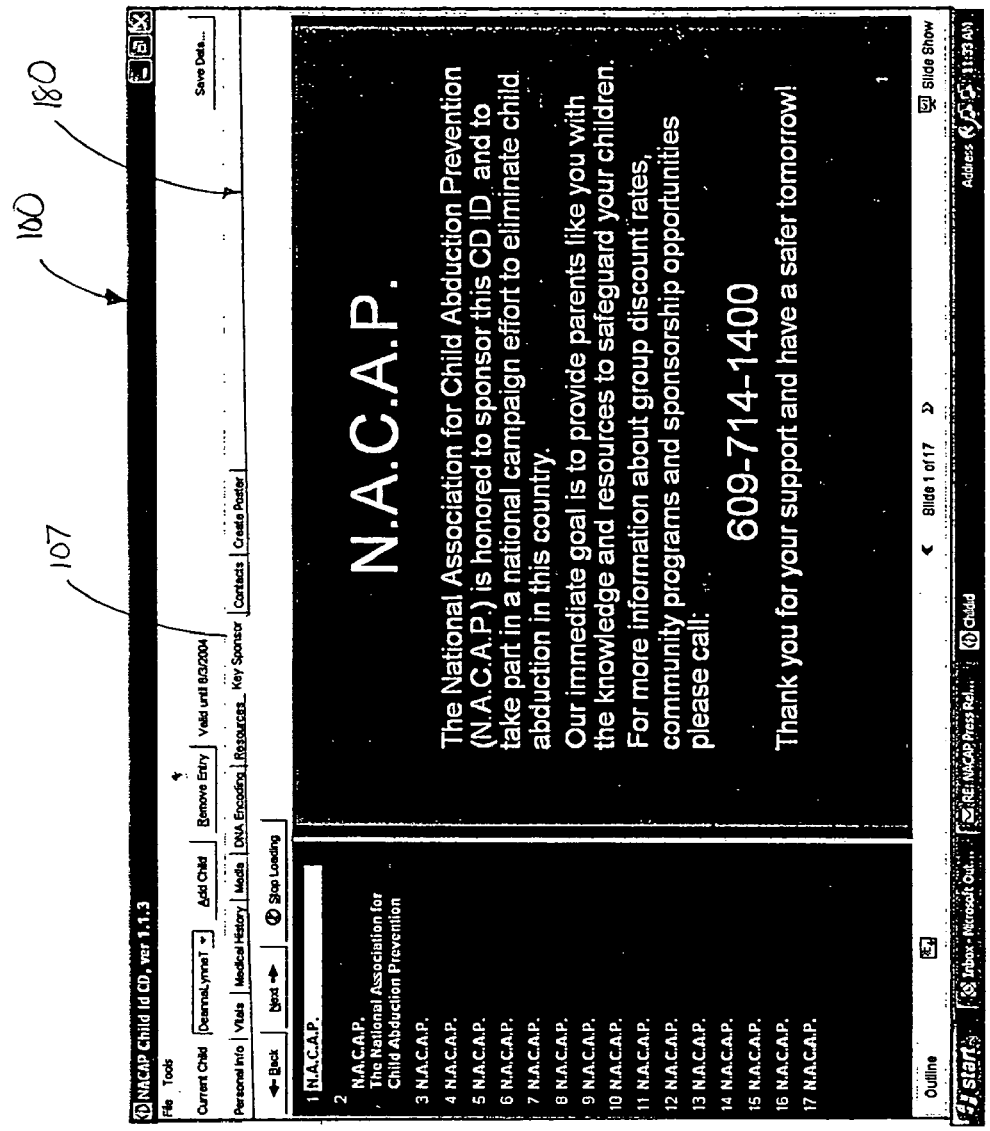
FIG. 9 illustrates the user interface displaying a key sponsor template according to an embodiment of the present invention.

FIG. 9 illustrates user interface 100 with key sponsor tab 107 activated, thereby displaying key sponsor template 180 in interface 100. Key sponsor template 180 displays an HTML file from any internal or external hard drive, into the software program. The "Key Sponsor" Tab can feature a corporate sponsor's web site as well.

Figure 10:
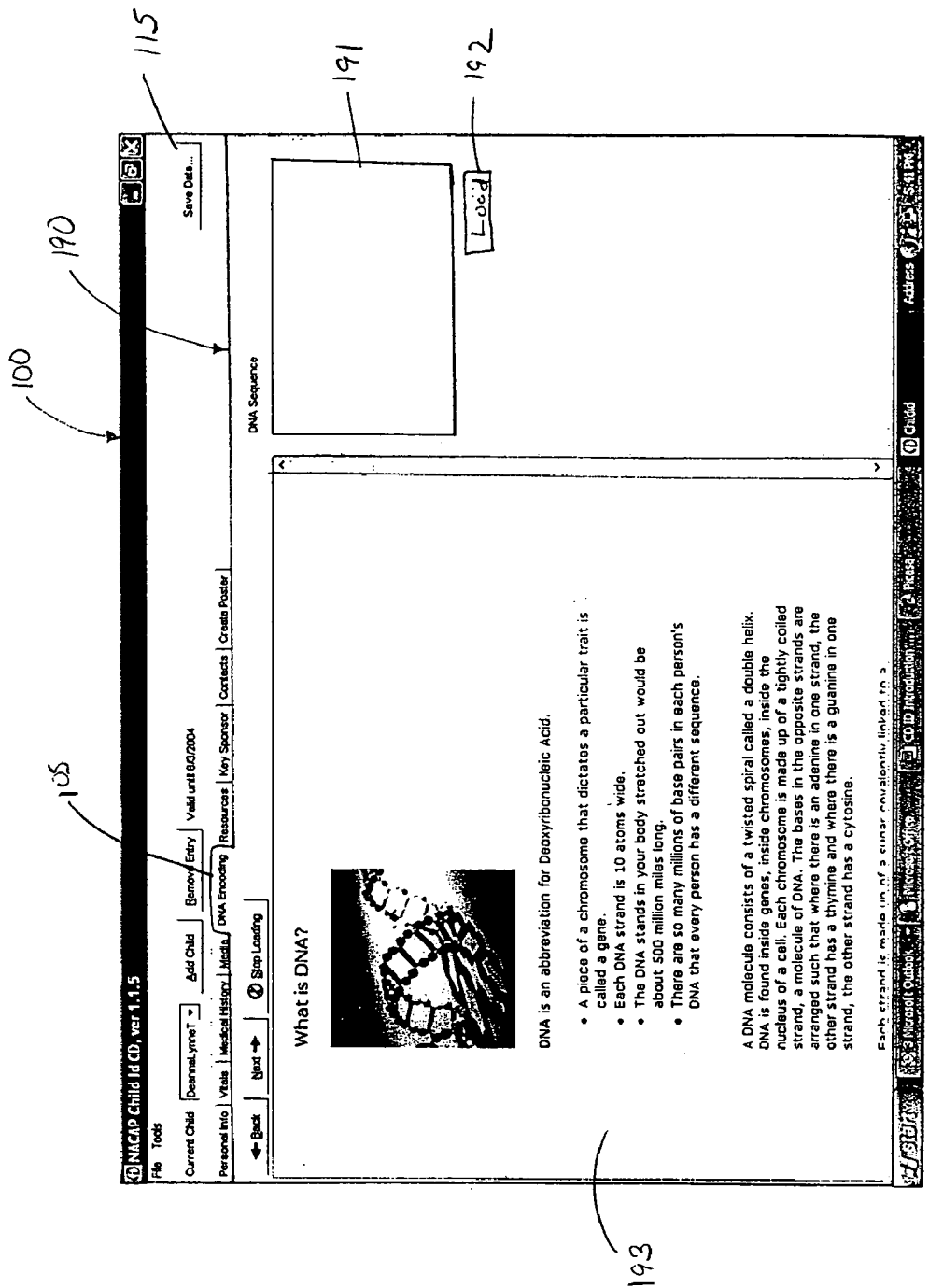
FIG. 10 illustrates the user interface displaying a DNA sequence importation template according to an embodiment of the present invention.

FIG. 10 illustrates user interface 100 with DNA encoding tab 105 activated, thereby displaying DNA sequence importation template 190 in interface 100. A user can load a file related to the DNA of a person by using the load button 192 which will display the DNA file in window 191. The DNA data file stored on the computer memory medium of USB key 10 by activating save button 115.

Figure 11:
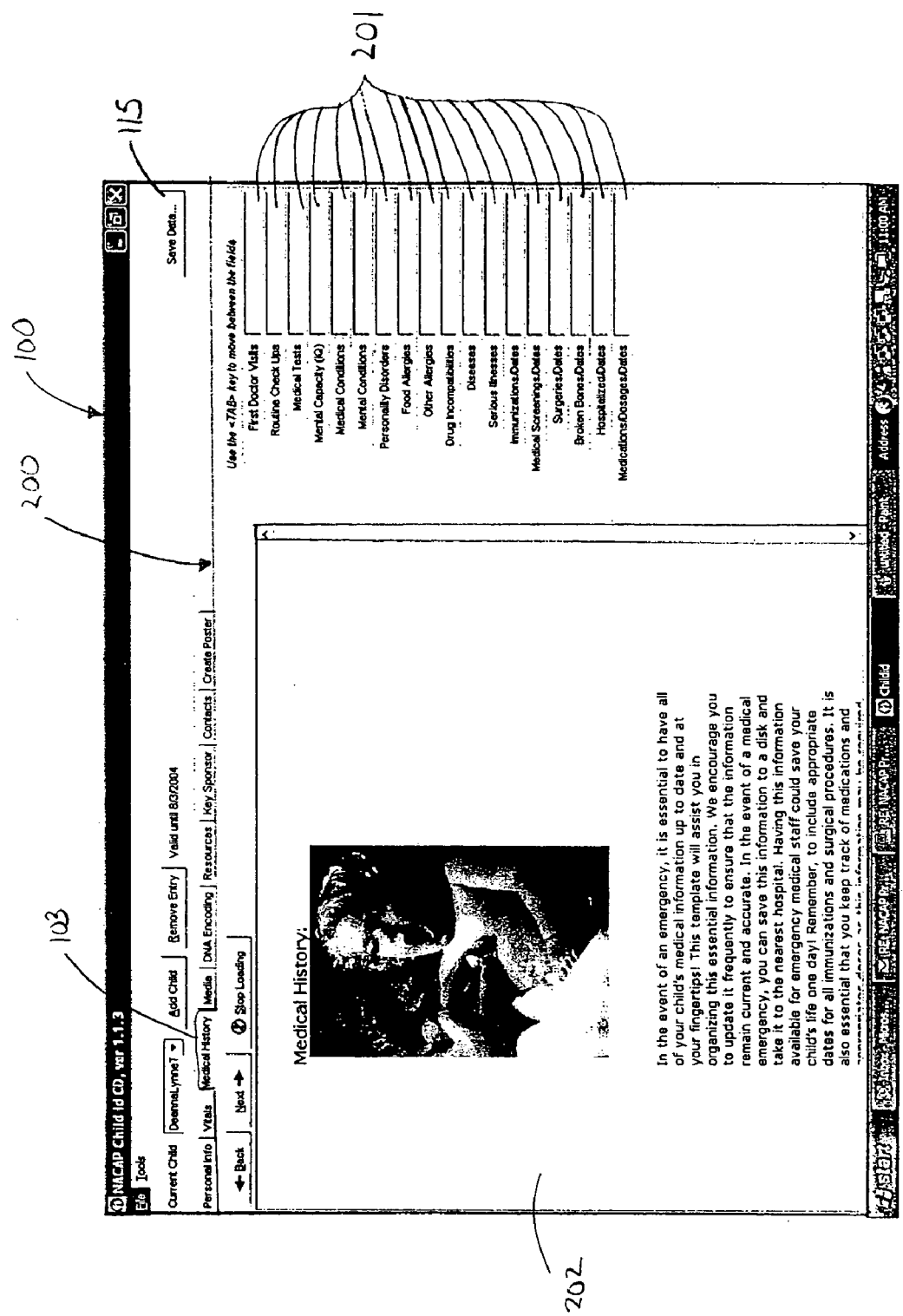
FIG. 11 illustrates the user interface displaying a medical history template according to an embodiment of the present invention.

FIG. 11 illustrates user interface 100 with medical history tab 103 activated, thereby displaying medical history template 200 in interface 100. Medical history template 200 comprises a plurality of data entry fields 201 for receiving data inputted by a user that relates to a child's or family member's medical history information, such as name, nickname, address, social security number, birth date, gender, nationality, native language, guardian's address, guardian's name, and guardian's phone number. This data is designed to comprehensively capture the child's basic medical history information. A user inputs the medical history data into data entry fields 201 via a keyboard, mouse, or other input device. The end user populates data entry fields 201 by depressing the tab key on a keyboard each time a field 111 is completed. The inputted data can be updated at any time.

When the user completes inputting the medical history data into all of the data entry fields 201, he/she activates save data button 115 located in the header of interface 100. When save data button 115 is activated, the medical history data that was inputted into data entry fields 201 by the user is transmitted and stored on the computer memory medium of USB key 10. Data is saved in a format so that it can be displayed in the corresponding data entry fields upon retrieval.

Figure 12:
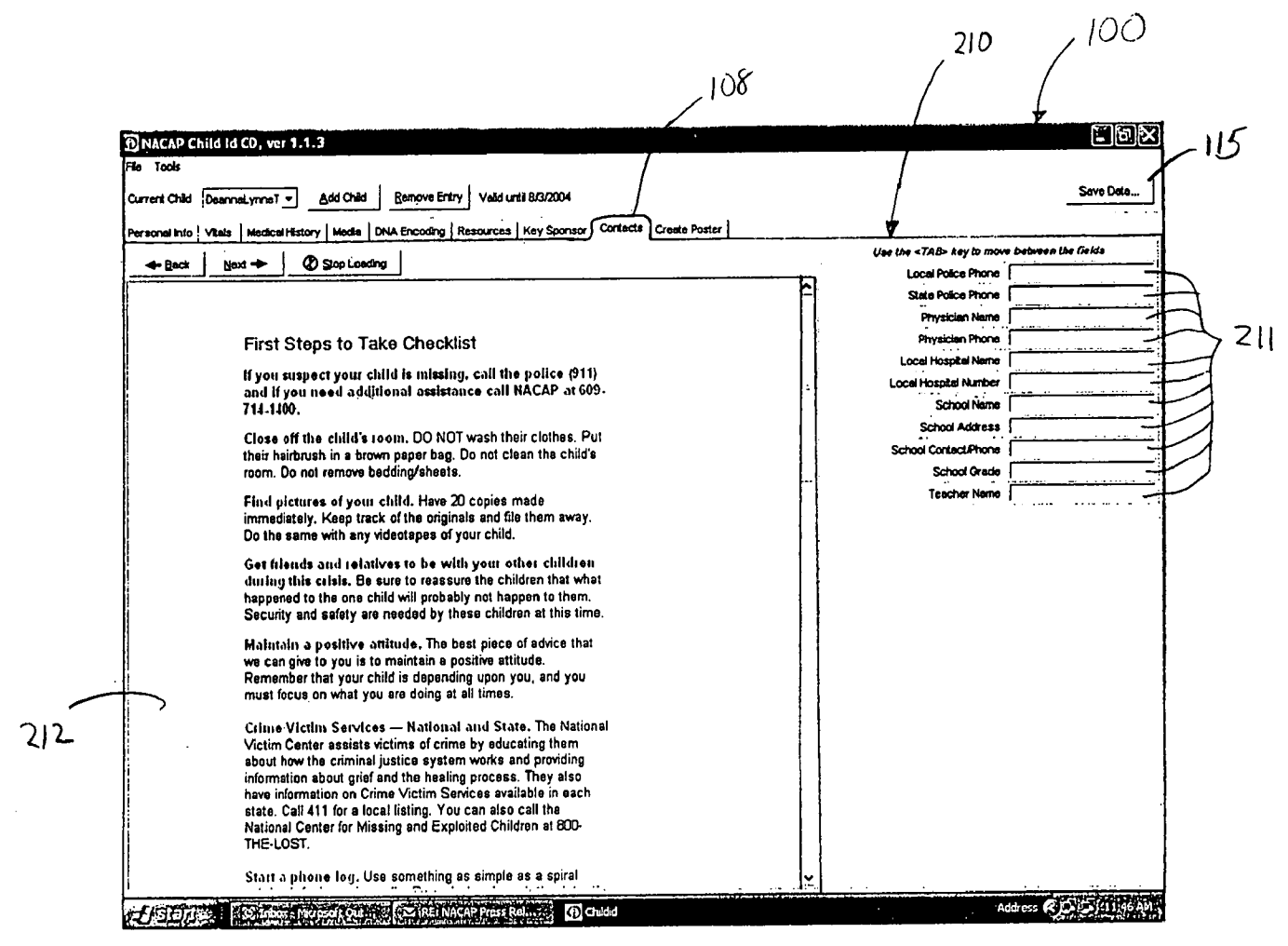

Referring now to FIG. 12, graphic user interface 100 is illustrated with contacts tab 108 activated, thereby contacts template 210 in interface 100. Contacts template 210 comprises a plurality of data entry fields 211 for receiving data inputted by a user that relates to important telephone numbers and contacts for future reference. All fields can be updated or changed at any time. The left panel 212 features a checklist of steps a parent/guardian should take in the event they loose a child. The left panel 212 is updateable simply by importing an html file into the computer memory medium of USB key 10. As discussed below inputted contact information, is used to populate/complete the missing person's poster illustrated in FIG. 14.

When the user completes inputting the contact data into all of the data entry fields 211, he/she activates save data button 115 located in the header of interface 100. When save data button 115 is activated, the contact data that was inputted into data entry fields 211 by the user is transmitted and stored on the computer memory medium of USB key 10. Data is saved in a format so that it can be displayed in the corresponding data entry fields upon retrieval.

Figure 13:
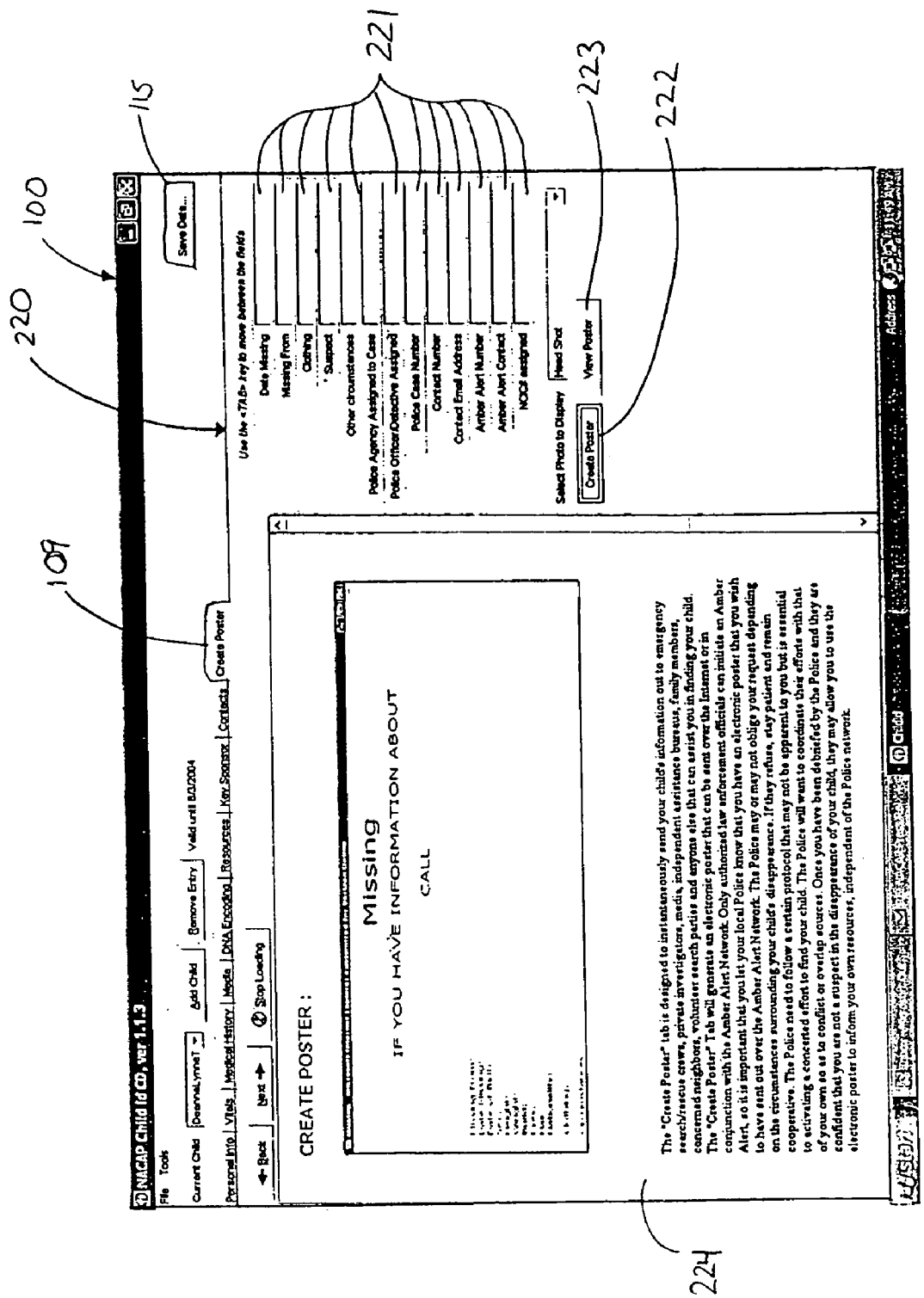
FIG. 13 illustrates the user interface displaying a create poster template according to an embodiment of the present invention.
Figure 14:
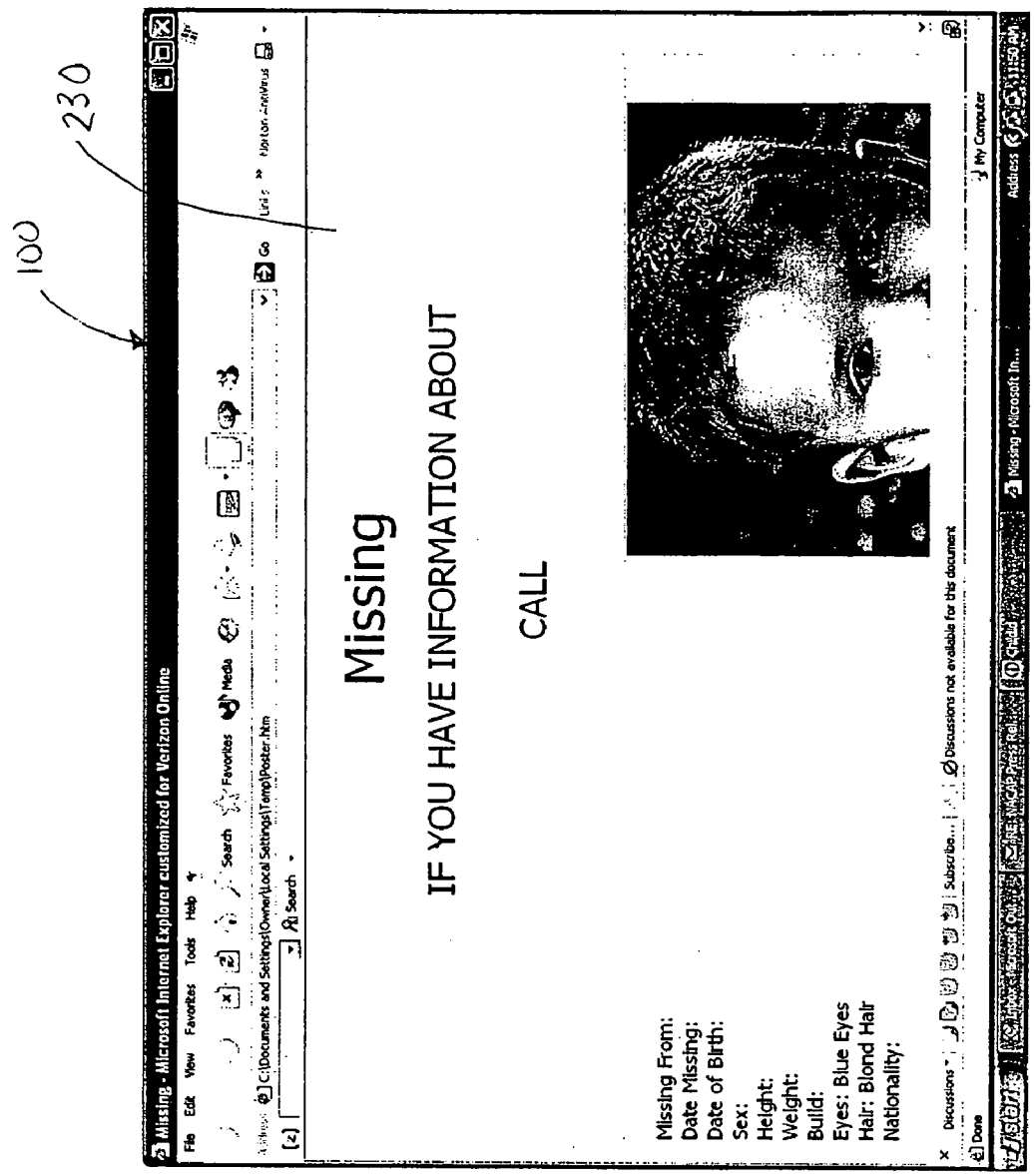
FIG. 14 illustrates the user interface displaying a poster template illustrating a poster created according to an embodiment of the present invention.

FIG. 13 illustrates user interface 100 with create poster tab 109 activated, thereby displaying create poster template 220 in interface 100. Create poster template 220 comprises a plurality of data entry fields 221 for receiving data inputted by a user that relates to all of the pertinent information concerning a child or other family member's disappearance. This data inputted into data entry fields 221 is also used to automatically populate/complete the Missing person's poster illustrated in FIG. 14. The template 220 is also used to input, store, and reference important numbers that will be used during the recovery of a missing child. Each of the relevant case and contact numbers are made easily accessible for the end user.

When the user completes inputting the data into all of the data entry fields 221, he/she activates save data button 115 located in the header of interface 100. When save data button 115 is activated, the data that was inputted into data entry fields 221 by the user is transmitted and stored on the computer memory medium of USB key 10. Data is saved in a format so that it can be displayed in the corresponding data entry fields upon retrieval.

Create poster template 220 further comprises create poster button 222 and view poster button 223. Upon a user activating create poster button 222, an electronic poster 230 (FIG. 1) is automatically created as single file based upon the data inputted by the user in the earlier filled data entry fields. The end user can pick which picture is to be depicted in the electronic poster 230 and ultimately view the poster 230 prior to distributing by activating view poster button 223.

Referring to FIG. 12, the electronic poster 230 seen by the end user when they push the view poster button 223. The illustrated electronic poster 230 is shown blank as no information has been imported in the data entry fields of the contact template or the create poster template. The contact number on the poster 230 is usually the Local Police and or the parent/guardian's home telephone number. The electronic poster 230 can be printed out and mailed or faxed or the poster can be electronically and distributed via e mail in an instant. Instantaneous transmission of poster images will save time and lives as it eliminates traditional typified by fax or direct mail distribution.

While the invention has been described and illustrated in sufficient detail that those skilled in this art can readily make and use it, various alternatives, modifications, and improvements should become readily apparent without departing from the spirit and scope of the invention. Specifically, while the invention is illustrated in the embodiment of a portable USB key, and portable device having a computer memory medium can be sued such as, any USB portable device (e.g., USB pens), key chain devices, CDs, floppy disks, and/or DVDs.

Moreover, while the invention is described specific to aiding in the recovery of missing or abducted individuals, the invention can also be used to aid in the proper medical treatment of an individual that may be unconscious, and in the case of a child, does not have the ability/knowledge to speak intelligently about their own medical condition. The same is the case with individuals with physical or mental impairments. These individuals stand a greater risk of being misdiagnosed, improperly medicated, or mistreated in an emergency medical situation. Thus, the software of the invention can be used in a number of situations and can be modified to store all or only a few of the categories of personal information.

What is claimed is:

1. A system for facilitating the identification or recovery of a missing person comprising:

a portable USB key comprising a computer memory medium and means for interfacing with a computer system having a display device;

a software program loaded on said computer memory medium, said software comprising means for receiving data indicative of a person's unique identification information, means for storing said received data on said computer memory medium, said computer memory containing data indicative of said person's unique identification information stored thereon, and means for displaying said stored data on said display device when said portable device is interfaced to the computer system;

wherein said unique identification information comprises personal and biological information selected from the group consisting of fingerprints, photographs, video, audio, DNA information, medical history, name, age, height, weight, eye color, and color of hair; and said means for receiving comprises a user interface comprising a plurality of templates having data entry fields in which a user can input said data.

2. The system of claim 1 wherein said means for storing comprises a save data button located within the user interface that when activated stores data that has been inputted into said data entry fields onto said computer memory medium.

3. The system of claim 1 wherein each of said templates further comprises a window for displaying information and/or instruction for completing that template.

4. The system of claim 1 wherein said user interface comprises a section displaying an expiration date for said stored data.

5. The system of claim 1 comprising a template having data entry fields for receiving data indicative of said person's name, nickname, address, social security number, birth date, gender, nationality, native language, guardian's address, guardian's name, and guardian's phone number.

6. The system of claim 5 wherein said template further comprises a window for displaying safety tips and/or a message from a sponsor.

7. The system of claim 1 comprising a template having data entry fields for receiving data indicative of said person's eye color, hair color, length of hair, hair style, facial hair, height, weight, build size, skin color, complexion, birth marks, identifying scars, identifying marks, physical disabilities, and mental disabilities.

8. The system of claim 7 wherein said template further comprises a window for displaying informational statistics relating to missing persons.

9. The system of claim 7 wherein said template further comprises an automated time and date stamp that is automatically updated when data is entered into the template and stored.

10. The system of claim 1 comprising a template having data entry fields for receiving digital photographs of said person, digital fingerprints of said person, digital video of said person, or digital audio clips of said person.

11. The system of claim 10 wherein said template further comprises a window for displaying instructions for importing said digital photographs, said digital fingerprints, said digital video, and said digital audio clips into said data entry field of said template.

12. The system of claim 11 wherein upon importation of said digital photograph into said data entry field, said digital photograph is automatically sized to fit in the corresponding data entry field.

13. The system of claim 1 comprising a template having a data entry field for receiving for receiving data indicative of a person's DNA sequence.

14. The system of claim 1 comprising a template having links to websites providing safety and/or abduction prevention information.

15. The system of claim 1 comprising a template having data entry fields for receiving data indicative of said person's medical history.

16. The system of claim 1 comprising a template having a window displaying a sponsor's message and/or information.

17. The system of claim 1 comprising a template having data entry fields for receiving data indicative of telephone numbers to contacts in the event of an abduction.

18. The system of claim 1 comprising a template for receiving missing information data.

19. The system of claim 18 further comprising means to automatically create an electronic poster based on said unique identification information and missing information data inputted into said data entry fields.

20. The system of claim 19 wherein upon creation, said electronic poster is saved on said computer memory medium as a single file that can be printed or electronically transferred.

21. The system of claim 1 further comprising a computer bard drive interfaced with said portable device and a display device.

22. The system of claim 1 wherein said means for displaying comprises a user interface comprising a plurality of templates having data fields, the stored unique identification information being displayed in data fields corresponding to the that characteristic.

23. A method of facilitating the recovery of a missing person comprising:

downloading a software program to a portable USB key comprising a computer memory medium and means for interfacing with a computer system having a display device, said software comprising means for receiving data indicative of a person's unique identification information, means for storing said received data on said computer memory medium, said computer memory containing data indicative of said person's unique identification information stored thereon, and means for displaying said stored data on said display device when said portable device is interfaced to the computer system;

wherein said unique identification information comprises personal and biological information selected from the group consisting of fingerprints, photographs, video, audio, DNA information, medical history, name, height, weight, eye color, and color of hair; and said means for receiving comprises a user interface comprising plurality of templates having data entry fields in which a user can input said data;

interfacing said portable device to a computer system having a display device; and displaying said person's unique identification information on said display device.

* * * * *